US011725173B2

(12) United States Patent
Cho et al.

(10) Patent No.: US 11,725,173 B2
(45) Date of Patent: Aug. 15, 2023

(54) HIGHLY EFFICIENT ORGANOID CULTURE DEVICE AND SYSTEM

(71) Applicant: CELLARTGEN INC., Seoul (KR)

(72) Inventors: Seung Woo Cho, Seoul (KR); Jin Kim, Seoul (KR); Yoonhee Jin, Seoul (KR); Ann Na Cho, Seoul (KR)

(73) Assignee: CELLARTGEN INC., Seoul (KR)

( * ) Notice: Subject to any disclaimer, the term of this patent is extended or adjusted under 35 U.S.C. 154(b) by 1085 days.

(21) Appl. No.: 16/448,889

(22) Filed: Jun. 21, 2019

(65) Prior Publication Data

US 2019/0390149 A1    Dec. 26, 2019

(30) Foreign Application Priority Data

Jun. 21, 2018  (KR) .................. 10-2018-0071538

(51) Int. Cl.
| | |
|---|---|
| *C12M 1/00* | (2006.01) |
| *C12M 1/06* | (2006.01) |
| *C12M 3/06* | (2006.01) |
| *C12N 5/071* | (2010.01) |
| *C12M 3/00* | (2006.01) |

(52) U.S. Cl.
CPC ............ *C12M 23/34* (2013.01); *C12M 21/08* (2013.01); *C12M 23/16* (2013.01); *C12M 23/58* (2013.01); *C12M 27/02* (2013.01); *C12M 27/16* (2013.01); *C12N 5/0697* (2013.01); *C12N 2513/00* (2013.01)

(58) Field of Classification Search
CPC ...... C12M 23/34; C12M 21/08; C12M 23/16; C12M 23/58; C12M 27/02; C12M 27/16; C12M 23/38; C12M 23/12; C12N 5/0697; C12N 2513/00
See application file for complete search history.

(56) References Cited

U.S. PATENT DOCUMENTS

| | | | |
|---|---|---|---|
| 2007/0099204 A1* | 5/2007 | Alexandre | ............. C12Q 1/686 435/6.15 |
| 2010/0213070 A1* | 8/2010 | Oki | .................... G01N 33/6872 204/275.1 |
| 2011/0236970 A1* | 9/2011 | Larsen | ................... C12M 23/12 435/395 |
| 2014/0227150 A1* | 8/2014 | Brettschneider | ........................... B01L 3/502738 156/272.8 |

OTHER PUBLICATIONS

Jin-Young Kim et al., "96-Well Format-Based Microfluidic Platform for Parallel Interconnection of Multiple Multicellular Spheroids", Journal of Laboratory Automation, 2015, pp. 274-282, vol. 20(3).

* cited by examiner

*Primary Examiner* — Liban M Hassan
(74) *Attorney, Agent, or Firm* — NKL Law; Jae Youn Kim

(57) ABSTRACT

The present invention provides an organoid culture device, comprising at least one first chamber for storing a culture medium; at least one second chamber for culturing an organoid; and a channel that interconnects adjacent chambers.

11 Claims, 18 Drawing Sheets

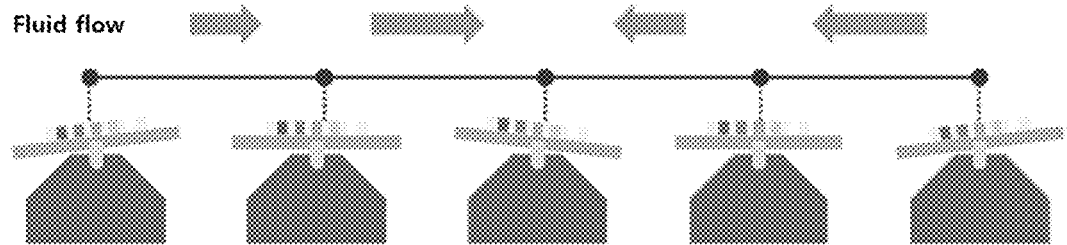
FIG. 3
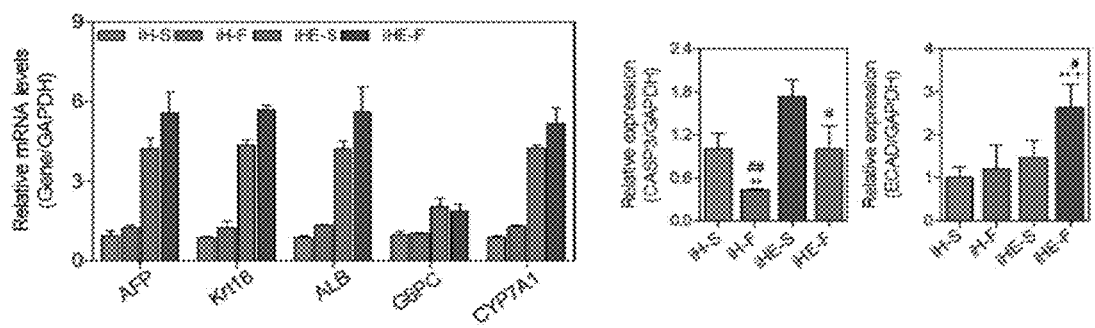
FIG. 4
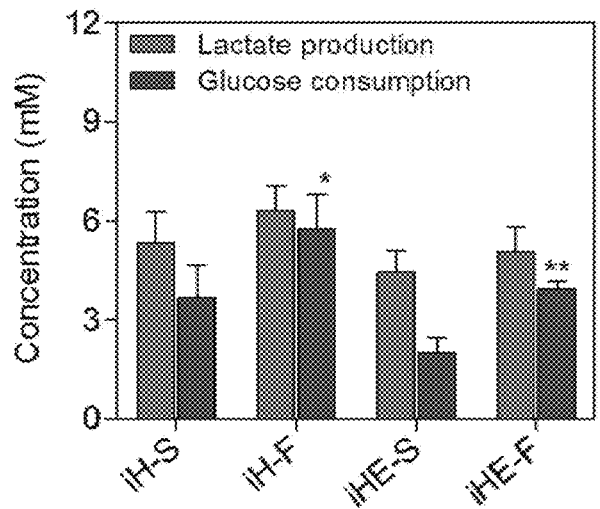 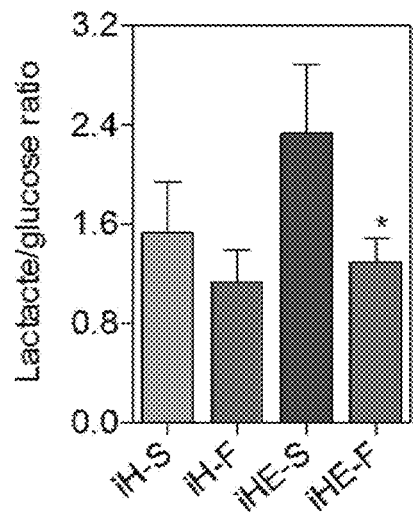
FIG. 5A  FIG. 5B

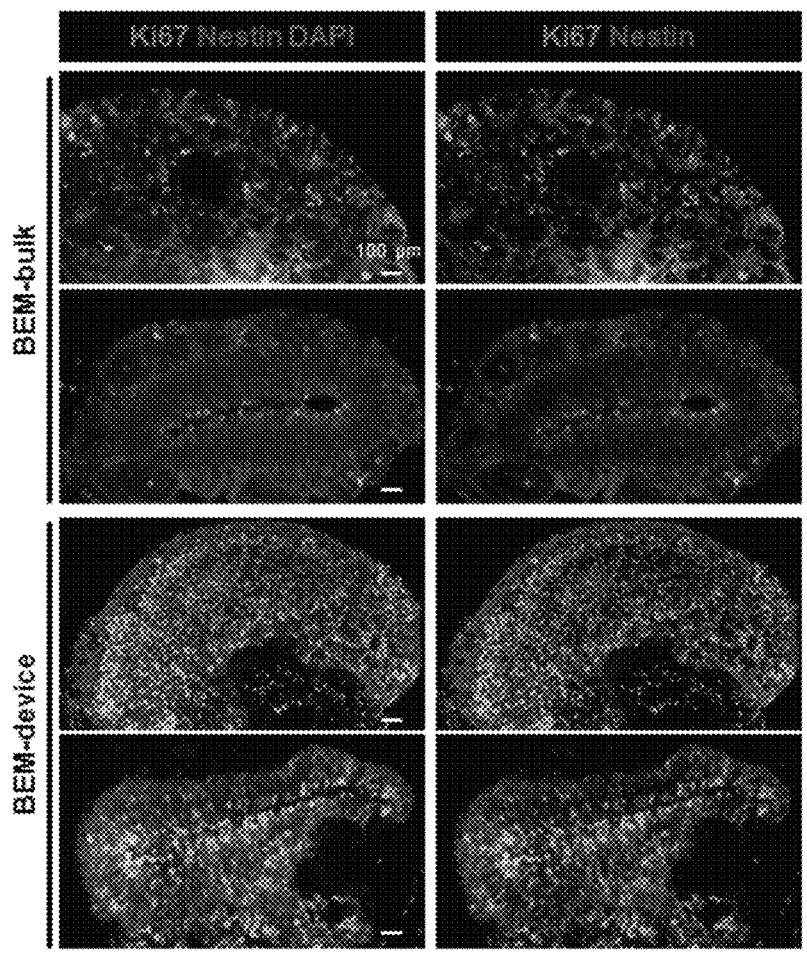 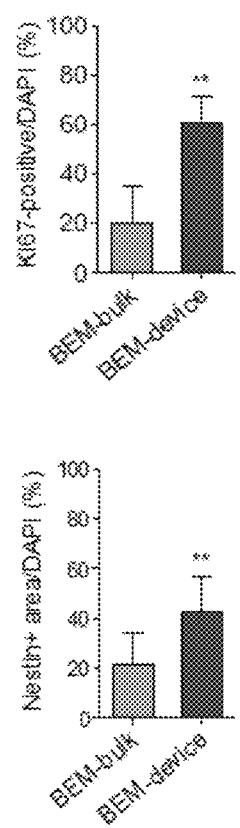
FIG. 9A
FIG. 9B

HIGHLY EFFICIENT ORGANOID CULTURE DEVICE AND SYSTEM

TECHNICAL FIELD

The present invention relates to a new type of culture platform capable of stably and efficiently culturing an organoid.

BACKGROUND ART

The technique for culturing a tissue-specific organoid is currently a cutting-edge field in stem cell research which is in the greatest spotlight, and the utilization thereof can be infinitely extended in the fields of regenerative medicine and new drug research such as an intractable disease model, a patient-customized drug screening platform, an in vitro model for new drug development.

Unlike the macro-scale culture, the technique for culturing cells using a microfluidic device is a technique that provides a microenvironment suitable for cells and precisely regulates culture conditions for cells which respond sensitively to the surrounding environment, and is recently gaining attention in the field of cell and tissue engineering.

However, unlike static culture, dynamic culture requires a fluid flow. Thus, for the dynamic culture, there is a need for complicated equipment such as a syringe pump or a hydraulic pump, and an expert.

In conventional organoid research, as a method used to impart a flow to the culture medium, there is a method of mounting a culture dish on an orbital shaker or a method of using a bioreactor such as a spinner flask. However, a different fluid flow is often given to each organoid. Thus, such methods can cause a severe batch-to-batch variation which has been pointed out as the biggest problem in organoid research.

In particular, the conventional organoid culture techniques have various problems in uniform organoid culture, formation of an organoid having high differentiation capability and functionality, and mass production.

The present inventors have developed a microfluidic device which is capable of generating a fluid flow without additional equipment by using a stirring device commonly used in a laboratory, and have identified that the device can enhance the survival, differentiation capability, and functionality of an organoid.

DISCLOSURE

Technical Problem

The present invention has been made to solve the above-mentioned problems of the prior art, and an object thereof is to contrive a microfluidic device which does not require separate additional equipment and is capable of precisely regulating a culture environment, and to provide a highly efficient organoid culture platform using the same.

Technical Solution

According to an aspect of the present invention, there is provided an organoid culture device, comprising at least one first chamber for storing a culture medium; at least one second chamber for culturing an organoid; and a channel that interconnects adjacent chambers.

In an embodiment, the first chamber and the second chamber may be adjacent to each other.

In an embodiment, the second chamber may have a lower height than the first chamber.

In an embodiment, the second chamber may have a smaller volume than the first chamber.

In an embodiment, the first and second chambers may have a cylindrical shape with a diameter of 5.0 to 15.0 mm.

In an embodiment, the device may further comprise a lid for the second chamber.

In an embodiment, the channel may have a width of 0.6 to 1.0 mm.

In an embodiment, the channel may have a height of 0.1 to 0.5 mm.

In an embodiment, the channel may be in a form in which one or more channels are stacked depending on volumes of the chambers.

In an embodiment, the organoid may be at least one organoid selected from the group consisting of brain, optic cup, kidney, liver, pancreas, neural tube, stomach, large intestine, prostate, breast, heart, salivary gland, endometrium, mammary gland, thyroid, tongue, lung, tumor, small intestine, and olfactory organoids.

According to another aspect of the present invention, there is provided an organoid culture system, comprising the culture device; a shaker; and a culture medium that is shared through the channel.

In an embodiment, the shaker may cause the device to make a swing motion.

According to still another aspect of the present invention, there is provided a method for culturing an organoid, comprising using the culture system.

Advantageous Effects

The culture system of the present invention enables culture of a highly functional organoid with high efficiency, and can be utilized for constructing various intractable disease models.

In a case where a tissue-specific organoid is uniformly mass-cultured on the basis of the culture system of the present invention and utilized for drug screening and new drug development processes, the success rate of new drug development can be greatly enhanced and the costs for new drug development can be remarkably decreased.

The culture system of the present invention can differ in shape and specification so as to be suitable for culture of different types of organoids having various shapes and sizes. Thus, the culture system of the present invention can be utilized for universal basic research, and is excellent in commerciality and product properties due to its universality.

The culture system of the present invention enhances differentiation capability, viability, and functionality of an organoid, and enables mass production, thereby contributing to the development of a source technology that can lead the field of next-generation cell therapy.

It should be understood that the effects of the present invention are not limited to the above-mentioned effects and include all effects which can be deduced from the detailed description of the present invention or the constitution of the invention described in the claims.

The above and other objects, features, and advantages of the present invention will become more apparent to those of ordinary skill in the art by describing in detail exemplary embodiments thereof with reference to the accompanying drawings, in which:

DESCRIPTION OF DRAWINGS

FIG. 3 illustrates a schematic diagram of the working principle of an organoid culture system according to an embodiment of the present invention;

FIG. 4 illustrates the results obtained by comparatively analyzing the difference of gene expression depending on a culture system through qPCR analysis;

FIGS. 5A and 5B illustrate the results obtained by comparatively analyzing the metabolism efficiency of a liver organoid depending on a culture system;

FIGS. 9A and 9B illustrate the results obtained by comparatively analyzing the survival and proliferation of a brain organoid depending on a culture system;

MODES OF THE INVENTION

Figure 1:
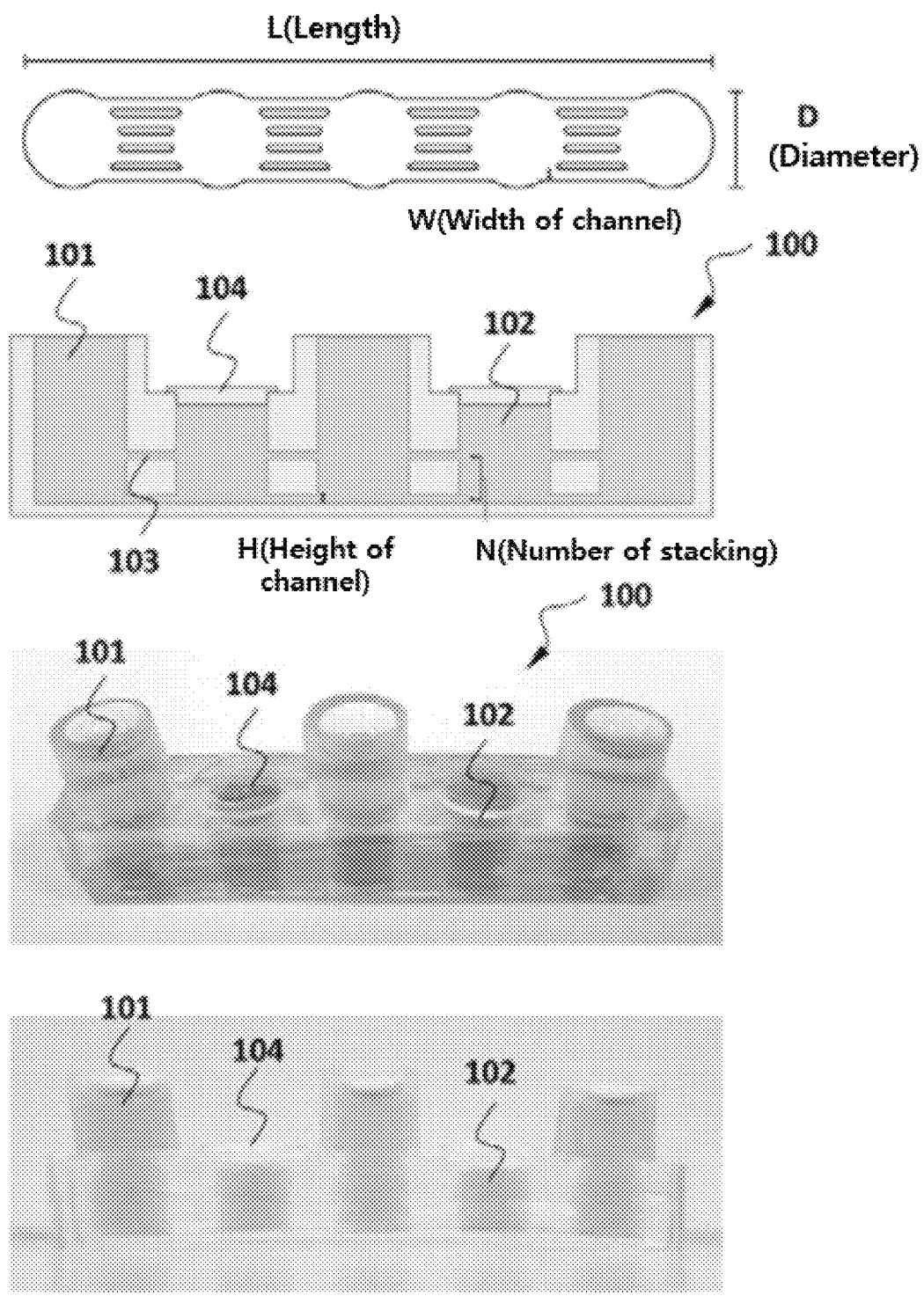
FIG. 1 illustrates a schematic diagram of an organoid culture device according to an embodiment of the present invention.

Hereinafter, the present invention will be described with reference to the accompanying drawings. The present invention may, however, be embodied in many different forms, and thus should not be limited to the embodiments set forth herein. In a case where a certain entity "comprises" a certain constitutional element, unless specifically stated otherwise, the case means that the entity may further include other constitutional elements rather than excluding the other constitutional elements.

Unless otherwise defined, practice of the present invention involves performing conventional techniques commonly used in molecular biology, microbiology, protein purification, protein engineering, DNA sequencing, and the field of recombinant DNA within the skill of those skilled in the art. The techniques are known to those skilled in the art and are described in numerous standardized textbooks and reference books.

Unless otherwise defined herein, all technical and scientific terms used have the same meanings as commonly understood by those skilled in the art.

Various scientific dictionaries that include the terms included herein are well known and available in the art. Although any method and material similar or equivalent to those described herein find use in the practice or testing of the present invention, some methods and materials are described. The present invention is not limited to particular methodology, protocols, and reagents, as these may vary depending upon the context to be used by those skilled in the art. Hereinafter, the present invention will be described in more detail.

According to an aspect of the present invention, there is provided an organoid culture device 100, comprising at least one first chamber 101 for storing a culture medium; at least one second chamber 102 for culturing an organoid; and a channel 103 that interconnects adjacent chambers.

The "organoid" refers to an ultraminiature body organ obtained by culturing cells derived from the tissue or pluripotent stem cells in a 3D form to produce a form such as an artificial organ.

The organoid is a three-dimensional tissue analog that contains organ-specific cells which originate from stem cells and self-organize (or self-pattern) in a similar manner to the in vivo condition. The organoid can be developed into a specific tissue by restricted element (for example, growth factor) patterning.

The organoid can have the original physiological characteristics of the cells and can have an anatomical structure that mimics the original state of a cell mixture (including all remaining stem cells and the neighboring physiological niche as well as limited cell types).

A three-dimensional culture method allows the organoid to be better arranged in terms of cell to cell functions, and to have an organ-like form with functionality and a tissue-specific function.

The organoid may be, but not limited to, at least one organoid selected from the group consisting of brain, optic cup, kidney, liver, pancreas, neural tube, stomach, large intestine, prostate, breast, heart, salivary gland, endometrium, mammary gland, thyroid, tongue, lung, tumor, small intestine, and olfactory organoids.

The culture device 100 includes a structure for efficiently culturing the organoid, and specifically may include at least one first chamber 101 for storing the culture medium, at least one second chamber 102 for culturing the organoid, and a channel 103 that interconnects adjacent chambers.

The first chamber 101 stores the culture medium and the second chamber 102 cultures the organoid through the stored culture medium. The adjacent chambers are interconnected through the channel 103 so that the culture medium can be shared throughout the culture device.

The chamber may provide a certain space for culturing an organoid, or a storage space for receiving the culture medium, and may be preferably open at the top.

The chamber may be formed of glass or a synthetic resin. However, without being limited thereto, the chamber may be made of various materials that do not affect the organoid or the culture medium.

The chamber may be made of a transparent, semitransparent, or opaque material, and may have different characteristics in consideration of culture environment or utilization. The culture device 100 is capable of efficiently culturing the organoid through the chamber.

The culture device 100 is capable of exchanging the culture medium in the chamber with a gentle flow through a specific structure, and is capable of culturing the organoid in a constant form and size without causing excessive stimulation or stress due to the flow of the culture medium.

The culture device 100 has a structure in which the culture medium is shared through a channel 103 that interconnects the chambers. It is sufficient that the culture device 100 can provide a flow to the culture medium by a constant vibration, and the size, structure, and shape thereof are not particularly limited.

However, the culture medium or the amount of oxygen required may vary depending on the type and nature of the organoid to be cultured.

Therefore, the size, diameter, or the like of the chamber may vary in consideration of culture environment for the organoid. In a case where a large amount of the culture medium is required, the volume or number of the first chamber 101 can be increased so as to provide a smooth supply of the culture medium.

In an embodiment, the first chamber 101 and the second chamber 102 may have the same shape and size, and the first chamber 101 and the second chamber 102 may be individually optimized in terms of diameter, volume, shape, and the like in consideration of the type or amount of an organoid.

According to an embodiment of the present invention, the second chamber 102 may have a lower height than the first chamber 101 (FIG. 1).

The first chamber 101 and the second chamber 102 may have different heights and the adjacent chambers may be connected to each other by the channel 103 to share the culture medium.

Specifically, the second chamber 102 may have a lower height than the first chamber 101, and the organoid may be stably cultured in the inner space of each second chamber 102.

Although the first chamber 101 stores the culture medium, the first chamber 101 is higher in height than the second chamber 102, and thus overflow of the culture medium due to vibration or shaking of the device can be prevented. Even though the first chamber 101 and the second chamber 102 have different culture medium levels, the culture medium level of the second chamber 102 may be maintained constant through the lid 104.

The arrangement and disposition of the first chamber 101 and the second chamber 102 are not particularly limited, and preferably, the first chamber 101 and the second chamber 102 may be adjacent to each other.

In an embodiment, the first chamber 101 and the second chamber 102 may be alternatively disposed, and the culture medium may be evenly distributed and shared.

In addition, the first chamber 101 and the second chamber 102 may be alternatively arranged in a single row, and may be configured in multiple rows in consideration of culture scale or use.

Figure 2:
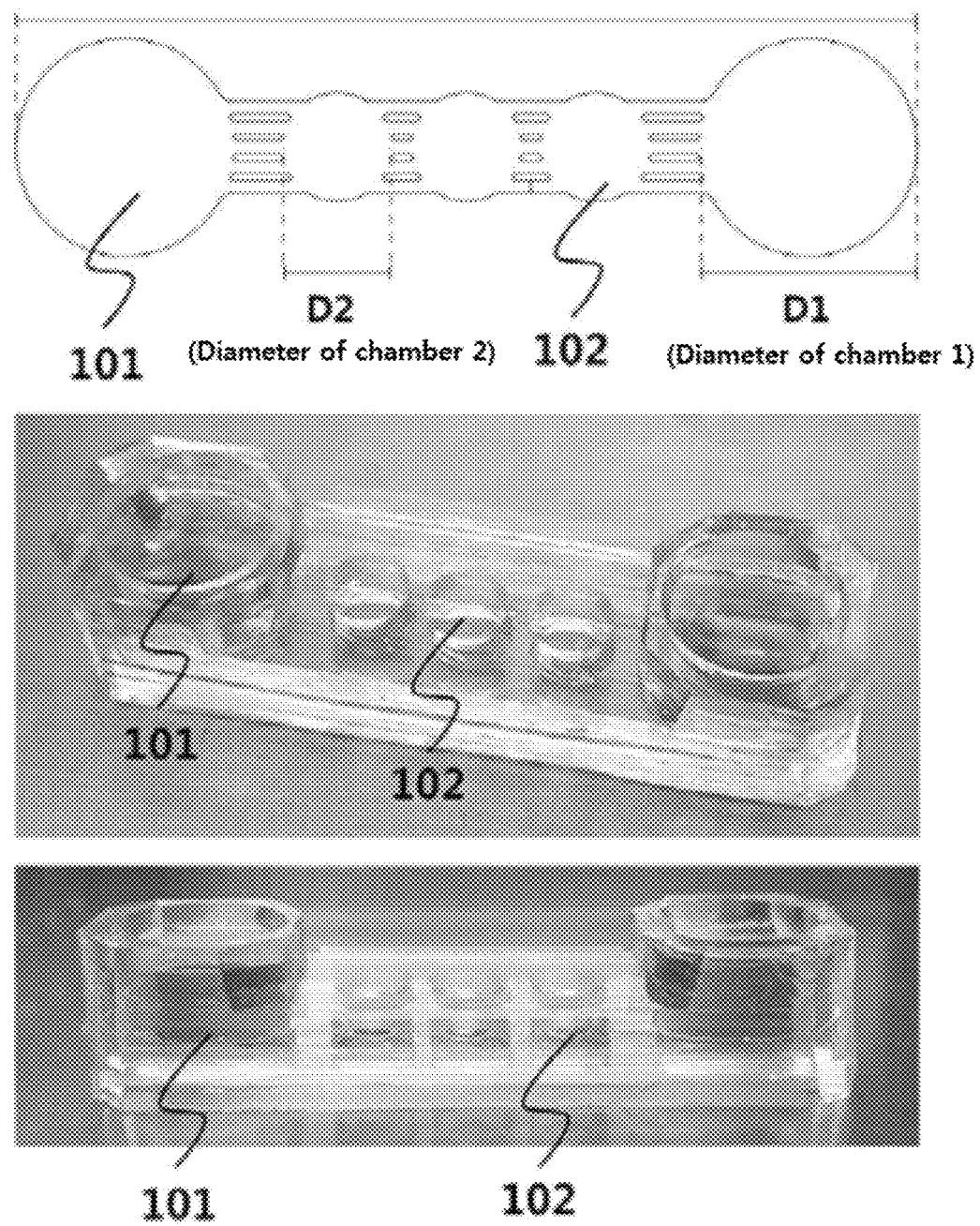
FIG. 2 illustrates a schematic diagram of an organoid culture device according to another embodiment of the present invention.

According to another embodiment of the present invention, the second chamber 102 may have a smaller volume than the first chamber 101 (FIG. 2).

It is sufficient that the culture device 100 can provide a flow to the culture medium by vibration or constant movement. Thus, the first chamber 101 may have an increased volume so that the culture medium can be smoothly supplied to the second chamber 102.

Referring to FIG. 2, since the first chamber 101 of the culture device 100 has the large chamber diameter and volume, a larger pressure (atmospheric pressure) is applied to the upper portion of the culture medium, and the flow of the culture medium between the first chambers 101 present at both ends of the device is further promoted by a motion of the culture device 100, so that the culture medium can be smoothly supplied to the second chamber 102.

Meanwhile, the organoid can be efficiently cultured through three-dimensional culture, and can be effectively cultured through a hydrogel, such as Matrigel, which is widely utilized in the art.

The "three-dimensional culture" provides an environment similar to actual tissue by excluding a process in which cells adapt to the two-dimensional environment of a flat plate, and can induce cell growth, differentiation, and function in vivo.

The three-dimensional culture can effectively mimic the actual in vivo tissue environment in an in vitro environment, and can improve the reliability of the results, and the stability and validity of experiments.

The "hydrogel" is a material in which a liquid that contains water as a dispersion medium is hardened, through the sol-gel phase transition, to lose fluidity and to form a porous structure. The hydrogel can be formed by causing a hydrophilic polymer that has a three-dimensional network structure and a microcrystalline structure to contain water and to be expanded.

The "Matrigel" is a protein complex (product name of BD Biosciences) extracted from Engelbreth-Holm-Swarm (EHS) mouse sarcoma cells, and may contain extracellular matrix components such as laminin, collagen, and heparan sulfate proteoglycan, and fibroblast growth factor (FGF), epidermal growth factor (EGF), insulin-like growth factor (IGF), transforming growth factor-beta (TGF-$\beta$), or platelet-derived growth factor (PDGF).

The shape of the first chamber 101 and the second chamber 102 is not particularly limited. The chambers may preferably have a cylindrical shape, and may have a diameter of 5.0 to 15.0 mm.

Since the organoid has different culture characteristics and rates depending on its nature, the chambers may have different shapes and volumes in consideration of culture environment.

The device may further comprise a lid 104 for the second chamber 102. The second chamber 102 is lower in height than the first chamber 101, and thus the culture medium can flow out to the outside due to vibration of the device. Therefore, the upper portion of the second chamber 102 can be closed through the lid 104.

The shape and size of the lid 104 are not particularly limited. The lid 104 may have the shape of a cap which closes the individual second chamber 102 or the shape of a cover glass with a large area which is capable of closing the adjacent second chambers 102 at the same time. The channel 103 allows the culture medium to move between the chambers. The cross-sectional area or shape of the channel 103 is not particularly limited and may vary in consideration of the culture characteristics of an organoid. Preferably, the channel 103 may have a width of 0.6 to 1.0 mm and a height of 0.1 to 0.5 mm.

In addition, the channel 103 may be in a form in which one or more channels 103 are stacked depending on volumes of the chambers. For example, in a case where the chambers have a large volume and the organoid to be cultured has a large volume, the channels 103 may be stacked to promote the movement of the culture medium.

According to another aspect of the present invention, there is provided an organoid culture system, comprising the culture device 100; a shaker; and a culture medium that is shared through the channel 103.

The "culture medium" is a culture medium for cells and is, at the same time, a medium for transporting nutrients, oxygen, or the like. The culture medium is capable of supplying nutrients, oxygen, or the like necessary for cells and removing waste.

The "shaker" is capable of imparting a dynamic flow to the culture medium by causing the culture device 100 to make a motion at a constant cycle.

It is sufficient that the shaker is capable of imparting a dynamic flow to the culture medium by changing the position of the device, and the range or form of the motion is not particularly limited.

Referring to FIG. 3, the shaker can cause the device to make a swing motion.

The "swing motion" refers to an operation mode of a mechanical device, indicating a motion in which the driving part does not rotate around an axis but reciprocates over a certain section.

The device makes a swing motion at a constant cycle. Thus, the culture medium in the device can make a reciprocating motion in the chamber at a constant cycle, and an environment in which the organoid can be stably cultured can be established.

According to still another aspect of the present invention, there is provided a method for culturing an organoid using the culture system.

The culture refers to a process of maintaining and growing cells under suitable conditions, and the suitable conditions may refer, for example, to the temperature at which the cells are maintained, nutrient availability, atmospheric $CO_2$ content, and cell density.

Appropriate culture conditions for maintaining, proliferating, expanding, and differentiating different types of cells are known in the art and are documented. Suitable conditions for the formation of the organoid may be conditions that facilitate or allow for cell differentiation and formation of a multicellular structure.

Hereinafter, the present invention will be further described by way of examples. However, it is apparent that the present invention is not limited by the following examples.

Experimental Example 1: Construction of Dynamic Culture System

A culture device composed of a first chamber and a second chamber was implemented. Depending on the nature of an organoid, designs which are different in the number of chambers as well as length, diameter, and width were selectively implemented.

The diameter D of the first chamber was increased or decreased in consideration of the size of the organoid, and the range of the flow rate was controlled by regulating the height H of the channel and the number N of the stacked channels depending on the required fluid flow intensity.

Conventional in-chip dynamic culture systems, which form a fluid flow through a syringe pump connected by a tube, not only essentially require additional equipment, but also have a limitation on the number of experimental samples due to the need for the chip and syringe to be connected 1:1. The conventional in-chip dynamic culture systems have insufficient convenience since proficiency is required in terms of utilization.

The organoid culture system of the present invention can simply form a fluid flow using a shaker, and is excellent in usability and expandability.

The organoid culture system of the present invention can provide various fluid flows depending on the speed and angle of the shaker. Since the culture medium is shared by the chambers in which the respective organoids are cultured, various organoids can be co-cultured to identify the effects on one another.

Experimental Example 2: Comparison of Gene Expression and Drug Reactivity

The gene expression of a liver organoid depending on culture conditions was quantified by qPCR analysis.

An induced hepatocyte (H) or an induced hepatocyte and a human umbilical vein endothelial cell (HUVEC) (HE) were encapsulated in a 3-dimensional hydrogel and cultured statically (S) or with a flow (F) in the device.

Referring to FIG. 4, it was identified that liver-specific gene marker expression is highest in the group which is co-cultured with vascular endothelial cells and to which a flow is given.

The flow groups (iH-F, THE-F) exhibited decreased expression of caspase-3 (CAPS3), a typical marker of apoptosis, as compared with the static groups (iH-S and THE-S).

In addition, ECAD (E-cadherin), a marker associated with cell-cell interactions, was expressed at the highest level in the THE-F group.

Experimental Example 3: Comparison of Metabolism Efficiency

Lactate production and glucose consumption of a liver organoid were quantified under various conditions (being co-cultured with vascular endothelial cells, or flow rate provided in the device).

Referring to FIGS. 5A and 5B, the groups (iH-F, THE-F) for which a dynamic culture had been performed using the device exhibited a decreased lactate/glucose concentration ratio as compared with the groups (iH-S, THE-S) for which a static culture had been performed.

The results suggest that dynamic conditions in the device increase the metabolism efficiency of the liver organoid.

Experimental Example 4: Comparison of Gene Expression and Drug Reactivity

Analysis of Transcripts Through RNA Sequencing

Genes which exhibit a two-fold or more difference in expression in a case of being compared with the iH-S group were denoted by a heat-map.

Figure 6A:
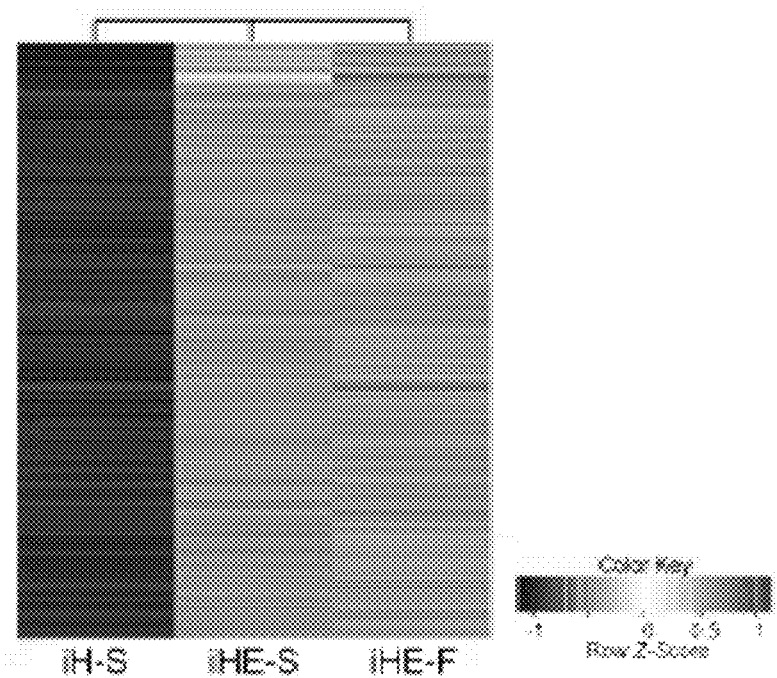
FIGS. 6A-6C to 8 illustrate the results obtained by comparatively analyzing the gene expression and drug reactivity of a liver organoid depending on a culture system.

Referring to FIG. 6A, the THE-S and THE-F groups exhibited similar gene expression patterns unlike the iH-S group.

Figure 6B:
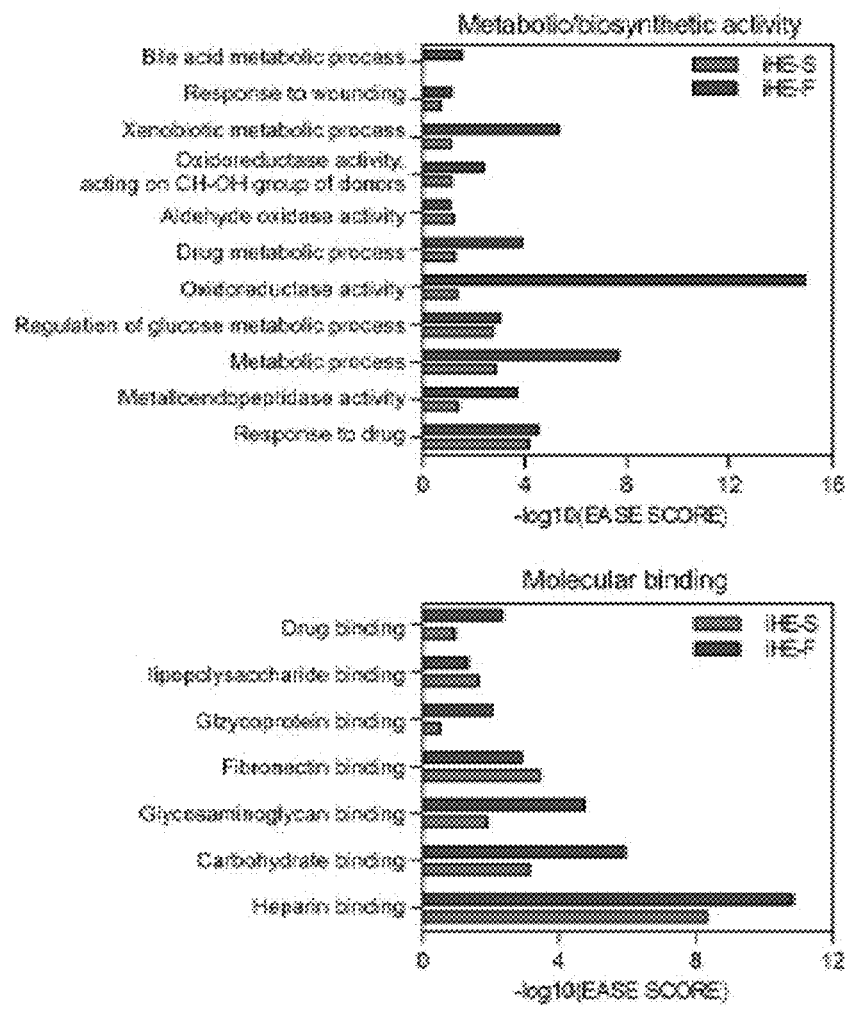
Figure 6C:
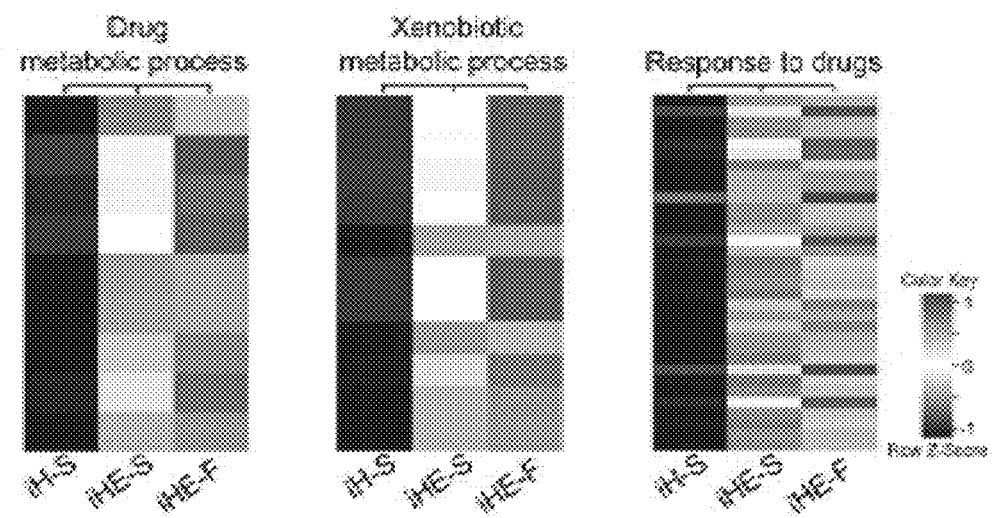

The gene ontology (GO) method was used to analyze the genes with a two-fold or more increase in expression. As a result, genes which are associated with metabolic/biosynthetic activity and molecular binding exhibited increased expression (FIG. 6B), and in particular, genes which are associated with a drug metabolic process, a xenobiotic metabolic process, and response to drugs exhibited increased expression (FIG. 6C).

Most of the GO terms in the THE-F group were increased to the highest level. These results suggest that an easier evaluation for drug reactivity and toxicity is made with the liver organoid which had been co-cultured with vascular endothelial cells under a flow culture condition in the culture system of the present invention.

Experiment for Evaluation of Drug Toxicity

Figure 7:
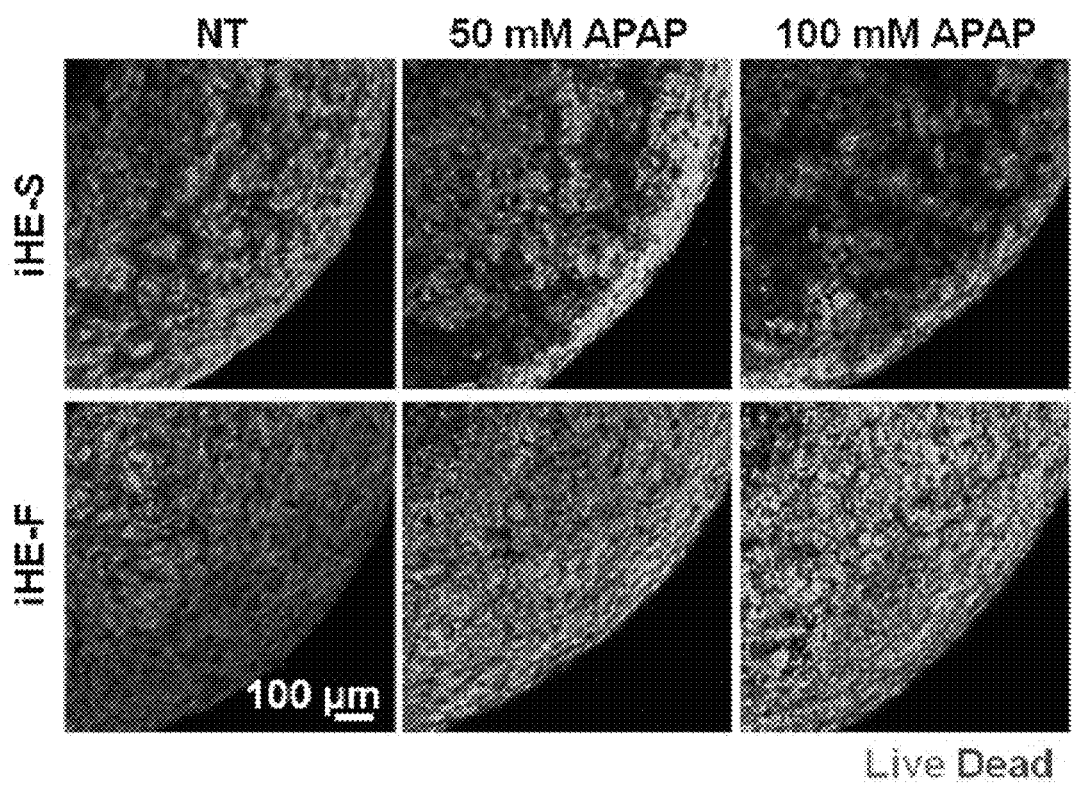

After the acetaminophen (APAP) drug, which is known to be hepatotoxic, and the HE group were incubated for 48 hours, an evaluation of hepatotoxicity was performed by a live/dead assay. As a result, more sensitive toxicity was observed in the flow group (FIG. 7).

That is, the THE-F group exhibits a more sensitive response at the same drug concentration than the THE-S group, and thus can be more usefully utilized for an evaluation of hepatotoxicity.

Experiment for Comparison of Drug Reactivity

An evaluation of hepatotoxicity of the APAP drug was performed. The distribution of intracellular glutathione (GSH) and reactive oxygen species (ROS) formation was identified by the monochlorobimane (mBCL) and dihydroethidium (DHE) assay in a case where the liver organoid of the THE-F group was cultured at various APAP (2 to 50 mM) concentrations.

Figure 8:
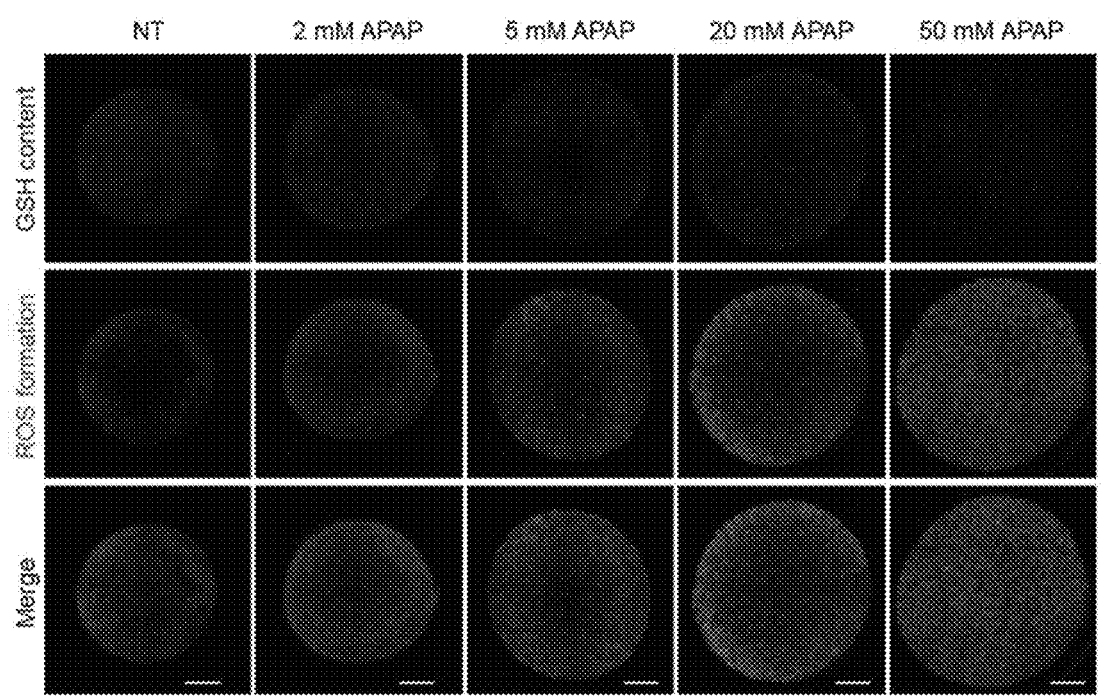

Referring to FIG. 8, the fluorescence of mBCL and DHE was lower and higher at higher concentrations, respectively. mBCL is a lipophilic GSH-specific probe and exhibits fluorescence at a specific frequency in a case of being bound to GSH.

These results indicate that the intracellular toxicity and damage of the liver organoid are increased with an increasing concentration of the APAP drug.

Experimental Example 5: Comparison of Survival and Proliferation

The characteristics of the brain organoid which is derived from human induced pluripotent stem cells and had been cultured in a dynamic device using a shaker or rocker, and the brain organoid which had been cultured in the existing culture system were analyzed.

After the brain organoid was cultured on a 3-dimensional culture platform for 30 days, and then analyzed by immunostaining.

Referring to FIG. 9A, through the immunostaining with Ki67, a cell proliferation marker, and nestin, a neural stem cell marker, it was identified that the proliferation of the brain organoid is promoted and the size growth and differentiation into a neuronal lineage are promoted.

Referring to FIG. 9B, the immunohistochemistry image-based quantitative analysis showed that in a case where the brain organoid is cultured in the device, the number of proliferating cells is significantly increased and the number of neural stem cells is also significantly increased.

In other words, the increased proliferative ability of the brain organoid cultured in the device of the present invention was identified by an increase in the number of neural stem cells.

Experimental Example 6: Comparison of Apoptosis

The brain organoid cultured in the device of the present invention and the brain organoid cultured in the existing culture system were incubated for 30 days, and then the degree of apoptosis was comparatively analyzed.

Figure 10A:
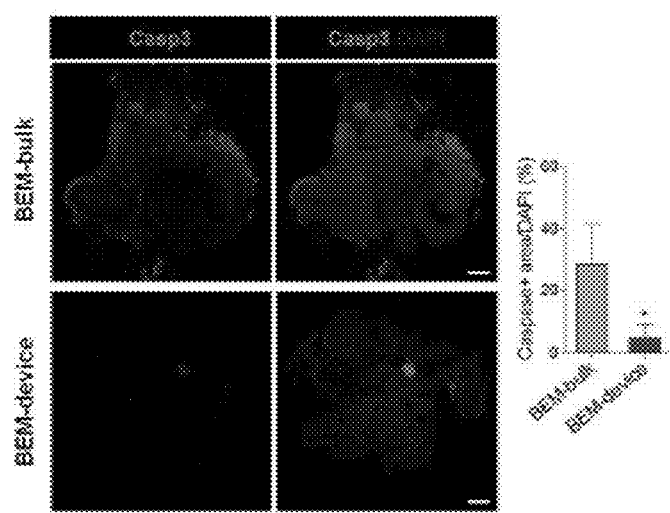
FIGS. 10A and 10B illustrate the results obtained by comparatively analyzing the degree of apoptosis and oxygen concentration of a brain organoid depending on a culture system.

Referring to FIG. 10A, the immunostaining and image-based quantitative analysis showed that decreased expression of the stained caspase-3 (casp3), an apoptosis marker, is exhibited in the brain organoid cultured in the device as compared with the existing culture system.

Figure 10B:
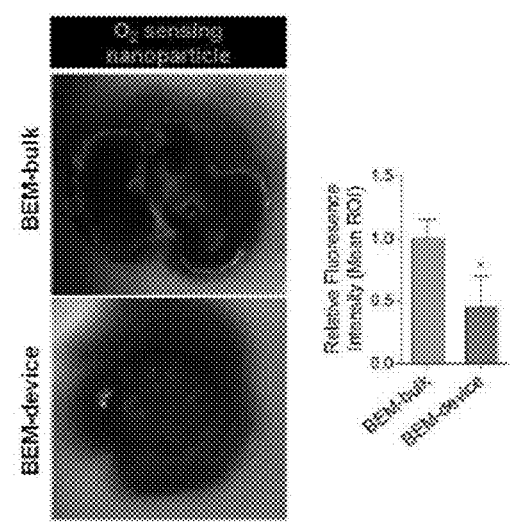

Referring to FIG. 10B, a relative oxygen amount in the brain organoid was analyzed through nanoparticles in which fluorescence expression decreases with an increasing oxygen amount. As a result, a large amount of oxygen was transferred into the brain organoid cultured in the device of the present invention.

The results suggest that the dynamic culture platform of the present invention can sufficiently supply oxygen into the organoid, and thus provide an environment in which apoptosis can be decreased.

Experimental Example 7: Comparative Analysis of Nutrient Supply and Waste Exchange The degree of nutrient supply and waste exchange in the culture system of the present invention and the existing culture system was comparatively analyzed.

Figure 11A:
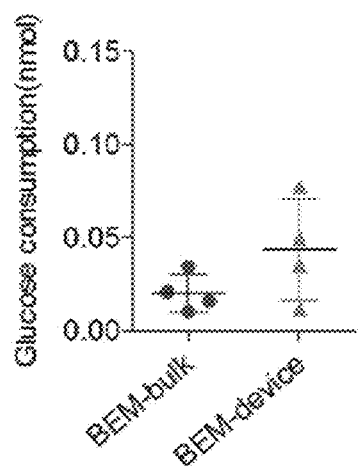
FIGS. 11A-11C illustrate the results obtained by comparatively analyzing the nutrient supply and waste exchange of a brain organoid depending on a culture system.

Referring to FIG. 11A, in a case of being compared with the brain organoid cultured in the existing multi-well plate system, it was analyzed that the brain organoid cultured in the device of the present invention exhibits a glucose consumption rate at a high level, indicating active metabolism of the brain organoid.

Figure 11B:
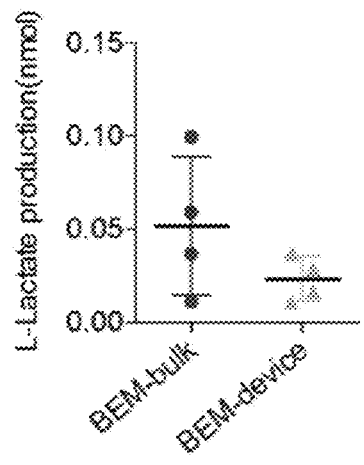

Referring to FIG. 11B, the brain organoid cultured in the device of the present invention exhibited decreased lactic acid (L-lactate) production, indicating that waste exchange actively occurs.

Figure 11C:
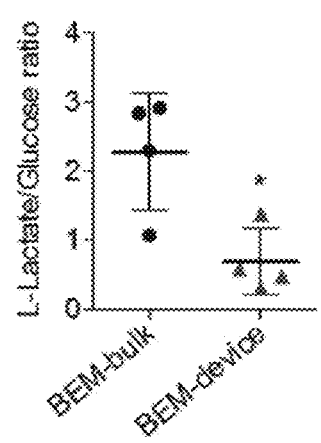

Referring to FIG. 11C, the ratio of lactate production to glucose consumption in the brain organoid was analyzed. As a result, nutrient supply and waste exchange were actively promoted in the culture system of the present invention.

Experimental Example 8: Comparative Analysis and Three-Dimensional Imaging Analysis of Neuronal Distribution The neuronal differentiation and distribution in the brain organoids of the culture system of the present invention and the existing culture system were comparatively analyzed.

Figure 12A:
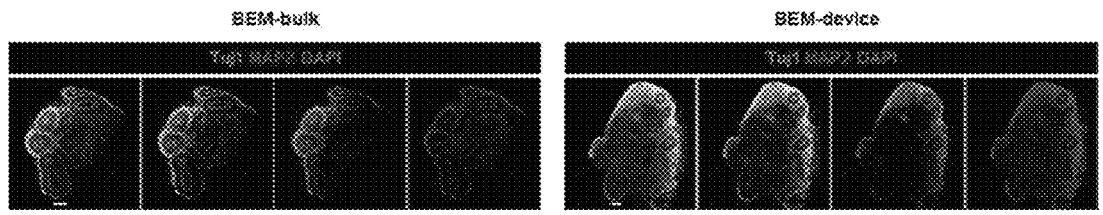
FIGS. 12A-12C illustrate the results obtained by comparatively analyzing the neuronal differentiation and distribution of a brain organoid depending on a culture system.

Referring to FIG. 12A, it was identified that in a case of the brain organoid cultured in the device of the present invention, increased expression of Tuj1 and MAP2, which are neuron biomarkers, is exhibited, and the development into a brain organoid is verified through the thickness of the layer in which mature cells are present, as compared with the existing culture system.

Figure 12B:
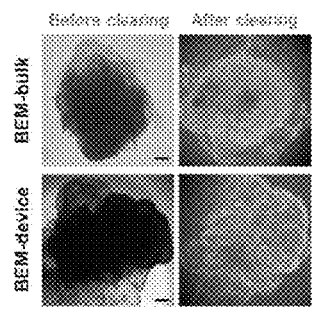

Referring to FIG. 12B, the degree of neuronal differentiation was analyzed three-dimensionally using a tissue clearing technique. Through the three-dimensional tissue clearing technique, the brain organoid was produced in such a way that the entire three-dimensional structure is easily imaged.

Figure 12C:
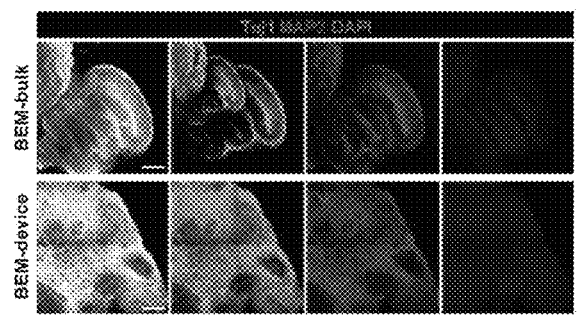

Analysis of the expression levels of the biomarkers (Tuj1, MAP2) showed that remarkably increased mature neuronal differentiation is exhibited in the brain organoid in the culture system of the present invention (FIG. 12C).

Experimental Example 9: Comparative Analysis of Cortical Layer Marker Expression in Brain Organoid The development of the cortical layer in the brain organoid was identified in the culture system of the present invention and the existing culture system.

Figure 13A:
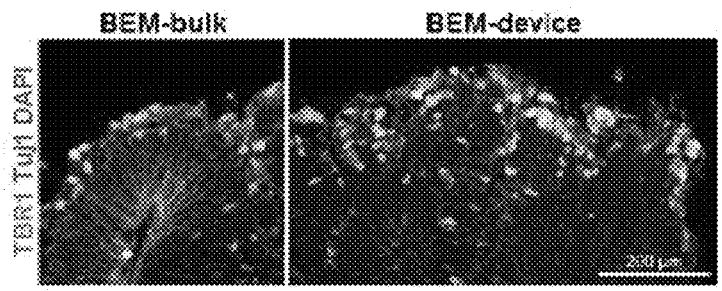
FIGS. 13A-13C illustrates the results obtained by comparatively analyzing the cortical layer marker expression level of a brain organoid depending on a culture system.

Referring to FIG. 13A, in the culture system of the present invention, development into TBR1+ cells that form the cerebral cortical layer VI was promoted, and development of the gyrus and sulcus was increased.

Figure 13B:
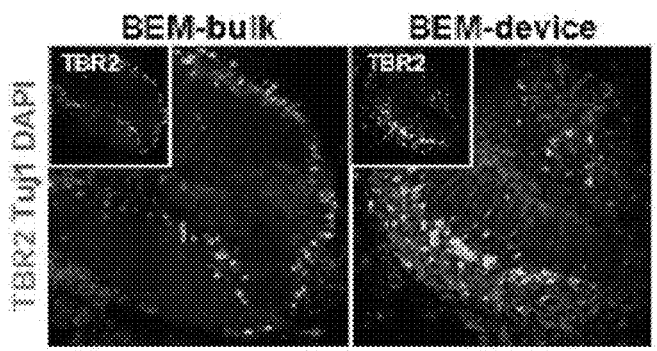

Referring to FIG. 13B, increased expression of TBR2, a biomarker of the cerebral upper cortical layer which constitutes the subventricular zone and the ventricular zone, was exhibited.

Figure 13C:
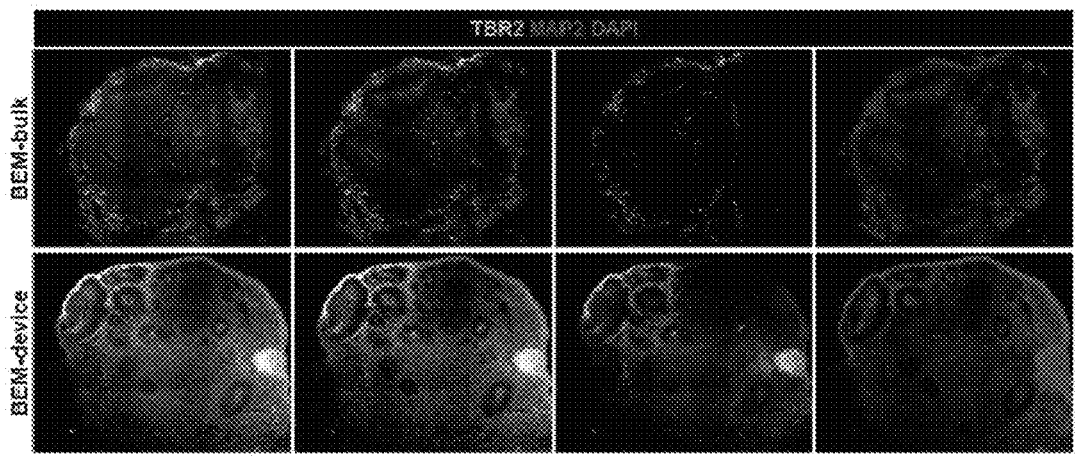

Referring to FIG. 13C, the cortical layer was overall widely formed in the brain organoid, indicating the development into a mature brain organoid.

Experimental Example 10: Comparative Analysis of Electrophysiological Functionality In order to identify the cortical layer development in the brain organoid, after performing culture for 60 days, electrophysiological functionality was analyzed by patch clamp analysis.

A larger activity of the neuronal sodium channel was exhibited in the culture system of the present invention (left side in FIG. 14B) as compared with the existing culture system (left side in FIG. 14A), and the differentiation into neurons with functionality was promoted.

Figure 14A:
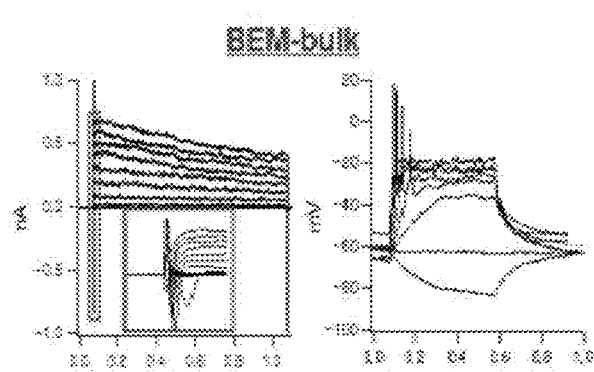
FIGS. 14A-14E illustrates the results obtained by comparatively analyzing the electrophysiological functionality of a brain organoid depending on a culture system.
Figure 14B:
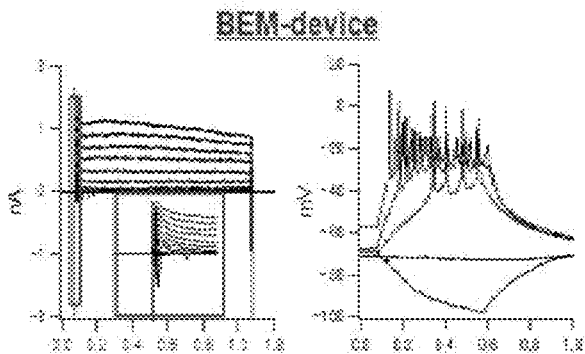
Figure 14C:
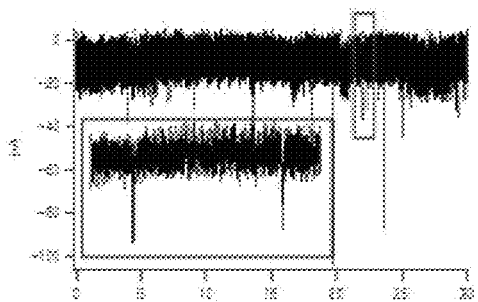
Figure 14D:
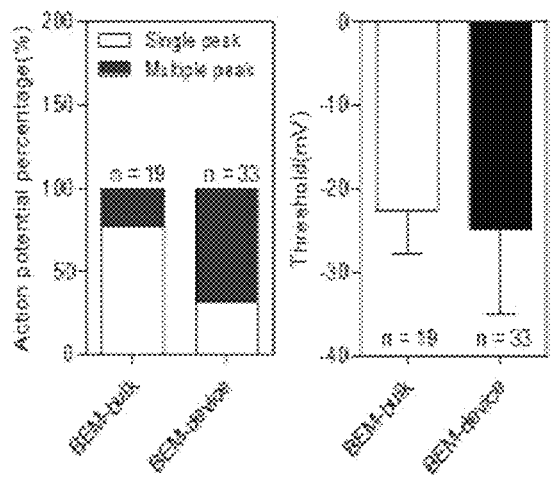
Figure 14E:
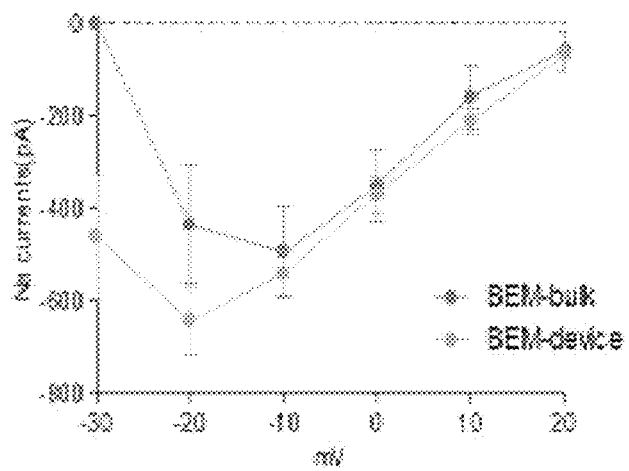
Figure 15A:
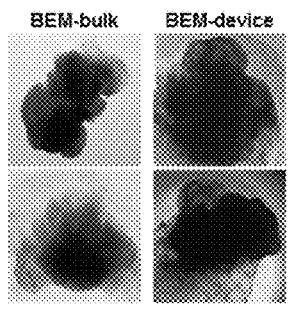
FIGS. 15A-15D illustrates the results obtained by comparatively analyzing the structure and size of a brain organoid depending on a culture system.
Figure 15B:
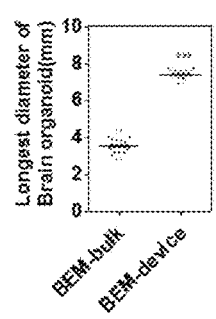
Figure 15C:
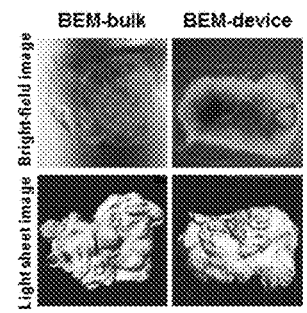
Figure 15D:
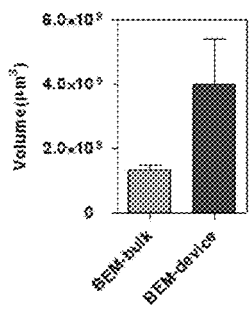

Referring to FIG. 14, differentiation into functionally highly mature neurons was identified by the increase of the action potential, the increased threshold value, and the decreased minimum value of the sodium current (right side in FIG. 14A, right side in FIG. 14B, FIG. 14D, and FIG. 14E).

In addition, in a case of the culture system of the present invention, unlike the existing culture system, an excitatory postsynaptic potential (EPSC), which is a neuronal inter-synaptic network, was identified (FIG. 14C).

Experimental Example 11: Structural Analysis of Brain Organoid

An analysis of cortical layer development in the brain organoid cultured for 60 days and a structural analysis thereof were performed.

Referring to FIGS. 15A-15D, the analysis using an optical microscope showed that in the culture system of the present invention, the brain organoid exhibits an increased size and exhibits the development of a wrinkled structure not only on the outer surface but also on the inside, so that the cortical layer of the actual brain was similarly recapitulated.

Light sheet microscopy was used to analyze the three-dimensional brain tissue-like organoid with high-resolution. As a result, in a case of the culture system of the present invention, a well-developed wrinkled structure of the cortical layer and an overall volume increase were exhibited, so that a brain organoid which realizes the tissue-like structure and size was formed (bottom in FIG. 15C and FIG. 15D).

Experimental Example 12: Analysis of Culture Environment Through Simulation

Fluid simulations were used to predict fluid flow and material transfer.

Figure 16:
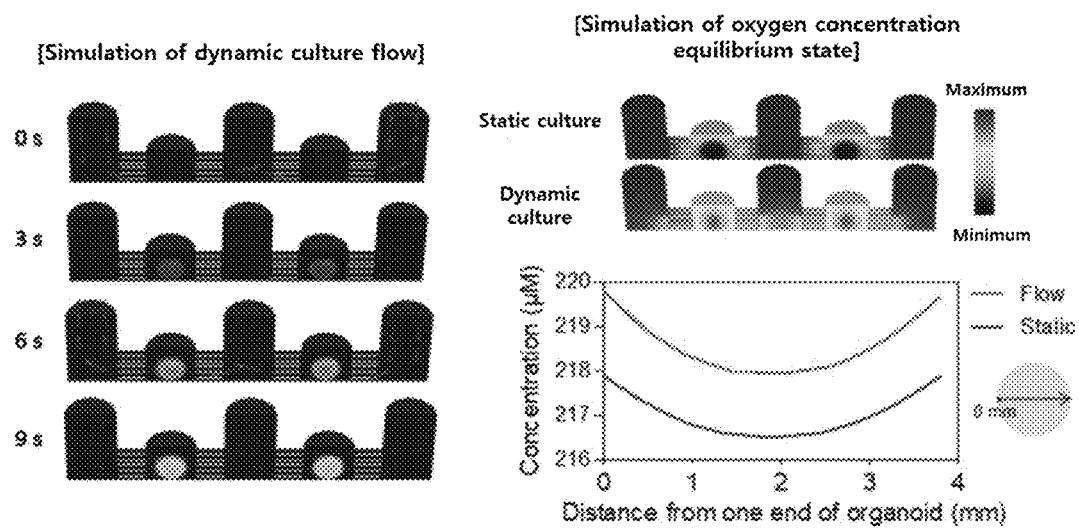
FIG. 16 illustrates the results obtained by comparatively analyzing the culture environment depending on a culture system through simulation.

Referring to FIG. 16, the dynamic culture system with a fluid flow and the static culture system were analyzed in terms of material transfer. As a result, in a case of the dynamic culture system, the exchange of oxygen and waste is promoted, and thus it is possible to improve the organoid culture in which the center part is killed as the size increases; and the fluid flow intensity can be controlled by changing the design.

Experimental Example 13: Utilization of Organoid Culture System

A system was constructed in which a large number (32) of organoids were able to be simultaneously cultured at high efficiency.

The system was configured to have the same specification as a 96-well plate format, and applied to a universal 96-well-based assay system such as a plate reader.

Figure 17:
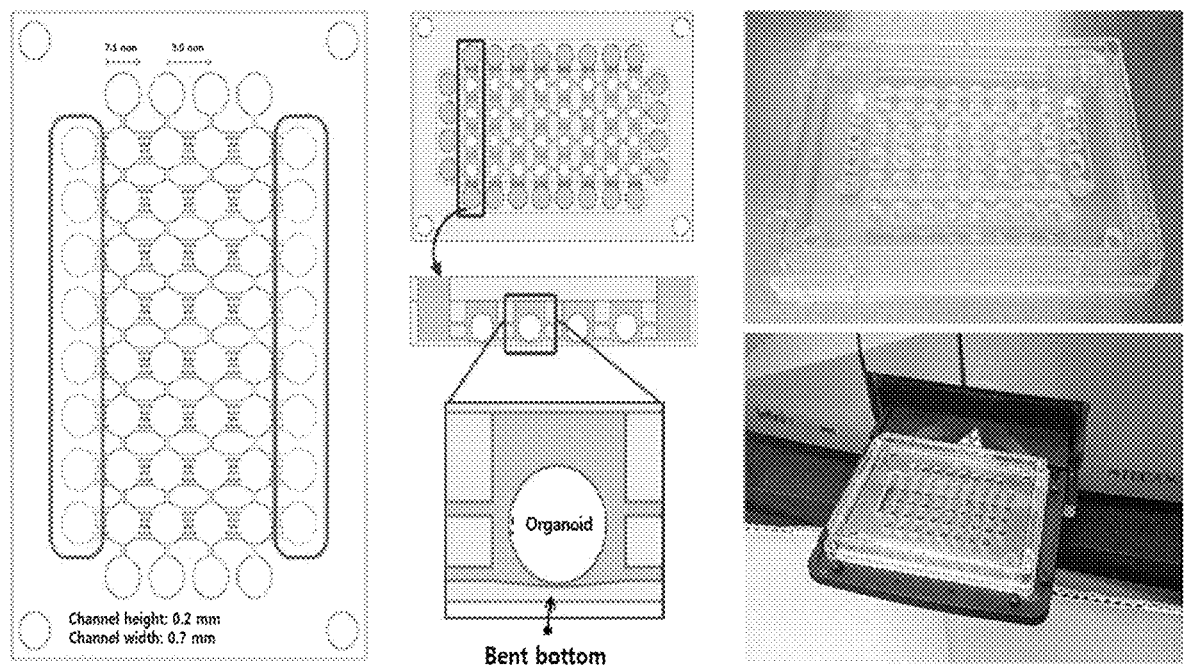
FIG. 17 illustrates a schematic diagram of a high-throughput multi-well organoid culture system according to an embodiment of the present invention.

Referring to FIG. 17, in a case of a 32-chamber based device, unlike a small-scale device focused on culture and observation, the bottom surface of each well is slightly bent to be applied to a quantitative analysis device. Thus, the 32-chamber based device was devised so that the organoid is located at the center of each well during the measurement using an instrument.

Figure 18:
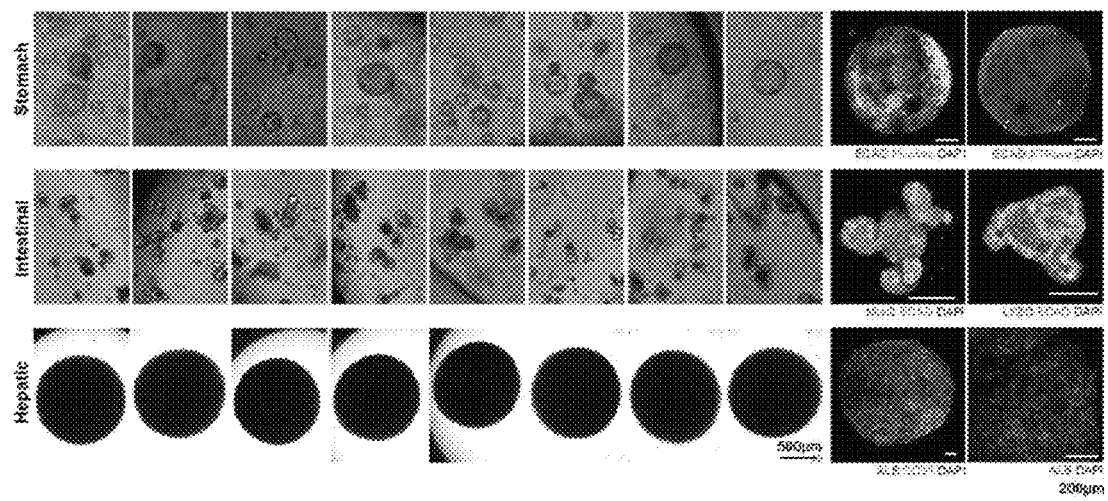
FIG. 18 illustrates the results obtained by observing the culture result obtained through a multi-well organoid co-culture system according to an embodiment of the present invention.

The induced hepatocyte-based liver organoid, stem cell-derived intestine organoid, and stomach organoid were co-cultured for 3 days using the culture system of the present invention (FIG. 18).

Immunostaining was used to observe the expression of tissue cell-specific markers in the co-cultured respective organoids (ALB=albumin, Ecad=E-cadherin, Lyso=lysozyme, P-pump=proton pump).

Co-culture of the induced liver organoid and the adult stem cell-derived intestine organoid was performed, and the interaction between the two organoids was analyzed.

Meanwhile, bile acid is produced from cholesterol in the liver, in which a primary bile acid formed in the liver is secreted into the intestines, and then is transformed into a secondary bile acid by intestinal microorganisms present in the intestines. Most of the bile acids reaching the intestines are reabsorbed into the liver by entero-hepatic circulation.

In a case where the bile acid is excessively secreted over the normal level, this is recognized by the enterocyte present in the intestines and the increased gene expression of FGF19 (FGF15 in mice) is exhibited.

The hepatocyte recognizes FGF19 and the gene expression of the cytochrome P450 enzyme CYP7A1, which is most important in the degradation of cholesterol into bile acids is suppressed, so that bile acid production is decreased.

Figure 19:
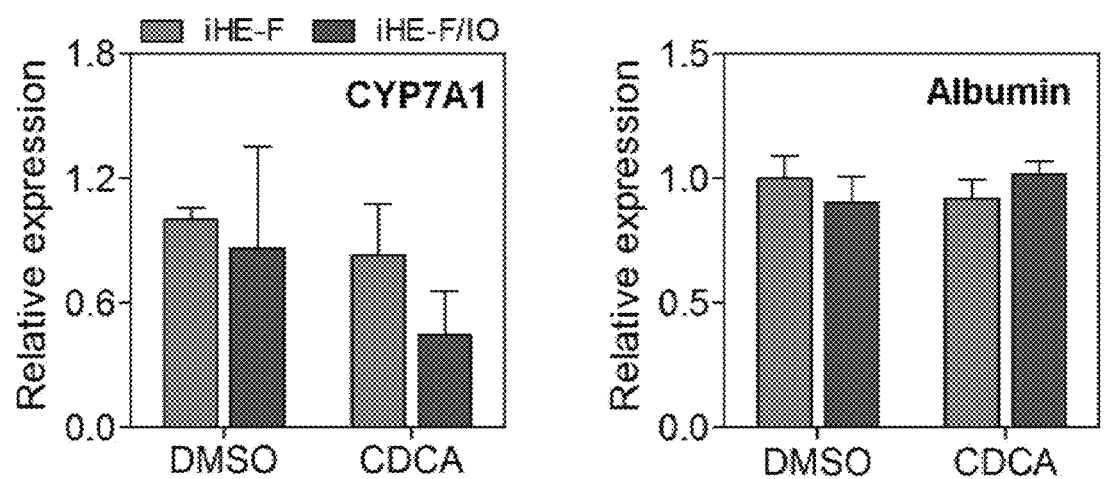
FIGS. 19 and 20A-20B illustrate examples of practical use of a multi-well organoid co-culture system according to an embodiment of the present invention.

Referring to FIG. 19, in a case where chenodeoxycholic acid (CDCA) (which is a hydrophobic bile acid that accounts for a large portion of bile acids) is present in the culture medium, as compared with the control in which the same volume of DMSO was added, the group in which the liver organoid alone was cultured exhibited no difference in the expression level of CYP7A1, whereas the group in which the liver organoid was co-cultured with the intestine organoid exhibited a decrease in the expression level of CYP7A1.

On the contrary, in a case of the albumin gene which is not related to the feedback loop that causes production of a proper amount of bile acid to be maintained, there was no difference in all conditions.

Therefore, the use of the culture system of the present invention makes it easy to co-culture the liver organoid and the intestine organoid, and enables intercellular interactions.

Figure 20A:
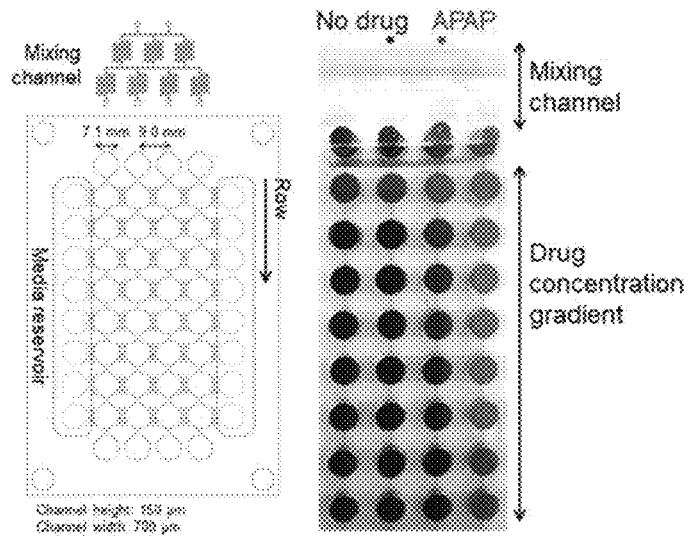
Figure 20B:
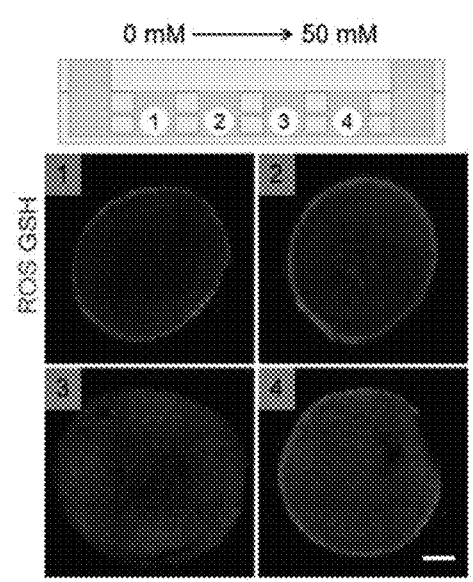

Experimental Example 13: Construction of Culture System Capable of Forming Drug Concentration Gradient and Toxicity Test Referring to FIGS. 20A-20B, in a case where a syringe pump and a mixing channel are connected to the culture device of the present invention, the desired drug concentration gradient is easily formed.

In a case where a blue solution is injected into the inlet port and an orange solution is injected into the other port using a syringe pump, a concentration gradient may be formed by the mixing channel.

Substantially, a medium containing 50 mM APAP was injected into the inlet port and a medium containing no APAP was injected into the other inlet port.

The liver organoid was cultured for 48 hours under the formed APAP drug concentration gradient. As a result, reactive oxygen species (ROS) were least produced in the cells (section 1) cultured on the medium containing no drug, and the cytotoxicity in the liver organoid increased as the drug concentration increased.

In other words, the organoid toxicity test depending on the drug concentration can be precisely and quickly performed by utilizing the culture system of the present invention.

The foregoing description of the present invention is for illustrative purposes, and it should be understood by those of ordinary skill in the art that various changes and modifications may be made without departing from the technical spirit or essential features of the present invention. It is therefore to be understood that the above-described embodiments are illustrative in all aspects and not restrictive. For example, each constitutional element described as a single entity may be implemented in a distributed manner. Likewise, constitutional elements described as distributed may also be implemented in a combined form.

The scope of the present invention is defined by the appended claims, and all changes or modifications deduced from the meaning and scope of the claims and their equivalents should be construed as being included within the scope of the present invention.

What is claimed is:

1. An organoid culture device, comprising:
   at least two first chambers for storing a culture medium;
   at least one second chamber for culturing an organoid; and
   a plurality of channels that interconnect the at least two first chambers and the at least one second chamber,
   wherein the at least two first chambers are arranged with a predetermined distance therebetween, and the at least one second chamber is provided between the at least two first chambers, and
   wherein the at least one second chamber has a smaller volume than the at least two first chambers,
   a bottom of the at least one second chamber includes a concave surface, and
   the plurality of channels are stacked interconnecting the at least two first chambers and the at least one second chamber.

2. The organoid culture device according to claim 1, wherein at least one of the at least two first chambers and the at least one second chamber are adjacent to each other.

3. The organoid culture device according to claim 1, wherein the at least one second chamber has a lower height than the at least two first chambers.

4. The organoid culture device according to claim 1, wherein the at least two first chambers and the at least one second chamber have a cylindrical shape with a diameter of 5.0 to 15.0 mm.

5. The organoid culture device according to claim 1, further comprising:
   a lid for the at least one second chamber.

6. The organoid culture device according to claim 1, wherein at least one of the plurality of channels has a width of 0.6 to 1.0 mm.

7. The organoid culture device according to claim 1, wherein at least one of the plurality of channels has a height of 0.1 to 0.5 mm.

8. The organoid culture device according to claim 1, where the organoid is at least one organoid selected from the group consisting of brain, optic cup, kidney, liver, pancreas, neural tube, stomach, large intestine, prostate, breast, heart, salivary gland, endometrium, mammary gland, thyroid, tongue, lung, tumor, small intestine, and olfactory organoids.

9. An organoid culture system, comprising:
   the device according to claim 1;
   a shaker; and
   a culture medium that is shared through the plurality of channels.

10. The organoid culture system according to claim 9, wherein the shaker causes the device to make a swing motion.

11. A method for culturing an organoid, comprising:
    using the culture system according to claim 9.

* * * * *